(12) United States Patent
Weidner et al.

(10) Patent No.: US 11,311,446 B2
(45) Date of Patent: Apr. 26, 2022

(54) EXOSKELETON FOR A HUMAN BEING

(71) Applicant: exoIQ GmbH, Bohlsen (DE)

(72) Inventors: Robert Weidner, Bohlsen (DE);
Jens-Peter Wulfsberg, Hamburg (DE);
Bernward Otten, Hamburg (DE);
Andreas Argubi-Wollesen, Hamburg (DE)

(73) Assignee: EXOIQ GMBH

( * ) Notice: Subject to any disclaimer, the term of this patent is extended or adjusted under 35 U.S.C. 154(b) by 777 days.

(21) Appl. No.: 16/084,557

(22) PCT Filed: Mar. 14, 2017

(86) PCT No.: PCT/EP2017/055998
§ 371 (c)(1),
(2) Date: Sep. 12, 2018

(87) PCT Pub. No.: WO2017/157941
PCT Pub. Date: Sep. 21, 2017

(65) Prior Publication Data
US 2019/0083350 A1 Mar. 21, 2019

(30) Foreign Application Priority Data
Mar. 14, 2016 (DE) .................... 10 2016 003 063.1

(51) Int. Cl.
*A61H 3/00* (2006.01)
*B25J 9/00* (2006.01)
*A61F 5/02* (2006.01)

(52) U.S. Cl.
CPC ............... *A61H 3/00* (2013.01); *A61F 5/026* (2013.01); *B25J 9/0006* (2013.01);
(Continued)

(58) Field of Classification Search
CPC .... B25J 9/0006; A61H 3/00; A61H 2003/007; A61H 2201/163; A61H 2201/165; A61H 2201/1638
See application file for complete search history.

(56) References Cited

U.S. PATENT DOCUMENTS 3,358,678 A   12/1967 Kultsar
3,467,421 A    9/1969 Bentley
(Continued)

FOREIGN PATENT DOCUMENTS

DE           307250      8/1918
DE      102011076843    12/2012
(Continued)

OTHER PUBLICATIONS

Korea Intellectual Property Office. Office Action for application 2018-7029584, dated Nov. 4, 2020. With machine translation.
(Continued)

*Primary Examiner* — Margaret M Luarca
*Assistant Examiner* — Nathan M Le
(74) *Attorney, Agent, or Firm* — Quarles & Brady LLP

(57) ABSTRACT

In order to avoid chronic damage for people performing physical labor and to support the execution of activities, an exoskeleton is provided as a support device with a device for implementing rotational and translational human movements. The exoskeleton, which is coupled to at least one body part of a person, comprises at least one man-technology interface, a device for implementing rotational and translational human movements, and an actuating unit which, under certain circumstances, is supplemented by a sensor system and a controller.

40 Claims, 9 Drawing Sheets

(52) U.S. Cl.
CPC .......... *A61H 2003/007* (2013.01); *A61H 2201/1207* (2013.01); *A61H 2201/1246* (2013.01); *A61H 2201/163* (2013.01); *A61H 2201/165* (2013.01); *A61H 2201/1616* (2013.01); *A61H 2201/1623* (2013.01); *A61H 2201/1638* (2013.01); *A61H 2201/1671* (2013.01); *A61H 2201/5061* (2013.01); *A61H 2201/5069* (2013.01)

(56) References Cited

U.S. PATENT DOCUMENTS

| | | | | |
|---|---|---|---|---|
| 3,608,541 | A * | 9/1971 | Hall | A63B 23/0244 600/594 |
| 5,282,460 | A | 2/1994 | Boldt | |
| 5,954,250 | A * | 9/1999 | Hall | A45F 3/047 224/262 |
| 6,113,642 | A | 9/2000 | Petrofsky et al. | |
| 6,436,065 | B1 * | 8/2002 | Mitchell | A61F 5/026 602/19 |
| 2003/0004473 | A1 | 1/2003 | Bonadio et al. | |
| 2005/0130815 | A1 * | 6/2005 | Abdoli-Eramaki | A61H 3/008 482/121 |
| 2007/0258671 | A1 | 11/2007 | Siemer et al. | |
| 2010/0036302 | A1 * | 2/2010 | Shimada | A61F 5/0102 602/16 |
| 2012/0172770 | A1 | 7/2012 | Almesfer et al. | |
| 2015/0316204 | A1 * | 11/2015 | Doyle | B25J 9/0006 248/118 |
| 2016/0206497 | A1 * | 7/2016 | Deshpande | B25J 9/0006 |
| 2017/0027735 | A1 * | 2/2017 | Walsh | A61F 5/0102 |
| 2019/0029910 | A1 * | 1/2019 | Kikutani | A61H 1/0292 |

FOREIGN PATENT DOCUMENTS

| | | |
|---|---|---|
| EP | 1364755 | 11/2003 |
| EP | 2796114 | 10/2014 |
| FR | 779284 | 4/1935 |
| JP | 3665879 B | 6/2005 |
| JP | 2012024557 | 2/2012 |
| JP | 2012239818 | 12/2012 |
| JP | 2013176429 A | 9/2013 |
| KR | 20130113063 A | 10/2013 |
| KR | 20140089826 A | 7/2014 |
| KR | 101539910 B1 | 7/2015 |
| WO | WO2011127421 | 10/2011 |
| WO | WO2014195373 | 12/2014 |

OTHER PUBLICATIONS

European Patent Office. Office Action for application 17711616.7. dated Mar. 1, 2022. With machine translation.

* cited by examiner

EXOSKELETON FOR A HUMAN BEING

This application represents the national stage entry of PCT International Application PCT/EP2017/055998 filed Mar. 14, 2017, which claims benefit of German Application 102016003063.1 filed Mar. 14, 2016, all of which is incorporated herein in its entirety by reference.

The invention relates to a wearable and controllable device (exoskeleton) for the avoidance of chronic musculoskeletal damage that may occur when performing work at or above head height, for example, in persons working in production and trade, which is characterized by a high fidelity of motion (coupling of rotational and translational degrees of freedom) due to a special configuration of the kinematic structure.

BACKGROUND OF THE INVENTION

Numerous applications relate to technical systems designed to support human activities, for example to improve quality and ergonomics. These systems are used in particular for an amplification of force and in different application contexts such as aerospace. Different parts of the body such as the arm or the entire body can be supported by them.

The subject matter of the invention can be identified in particular by a much more intensive and closer, and not only temporary, coupling between the kinematic structure and the human body part, in particular the shoulder. This basic condition leads to a much slimmer and more compact device design. This can be seen from the fact that, in a compact device, not only the rotational but the translational degrees of freedom are reflected as well. A significantly improved fidelity of motion can be realized hereby.

SUMMARY OF THE INVENTION

It is the task of the invention to provide a device that supports a human being in his movements, in particular when he is working overhead.

The task is solved by the features of the independent claim. Further exemplary embodiments of the invention are described in the dependent claims and the description below.

A first aspect of the invention relates to an exoskeleton for a human being. The exoskeleton comprises:
 a shoulder member;
 at least one arm support;
 a pelvic support member; and
 a back part, with a first end and a second end.

The back part comprises at least a first flexible-area back member with a first and a second part and at least a first stiffening means, whereby the first flexible-area back member is arranged so that its first end faces in the direction of the first end of the back part and its second end faces in the direction of the second end of the back part. The first end of the back part is fastened to the shoulder member, and the second end is fastened to the pelvic support member. The armrest is articulated directly or indirectly to the shoulder member. The first stiffening means is designed so that it specifically stiffens the first flexible-area back member in a bending direction.

To support a user, or respectively a human being in his activities, in particular when working overhead, the invention provides for an exoskeleton. This exoskeleton may both support and relieve the user by specifically transferring the force arising at the user's arm into the user's back and pelvis. Furthermore, an actuator may actively support the user in his movements.

The exoskeleton according to the invention may be substantially comprised of three modules. The first module to be referenced is the shoulder arrangement to replicate the user's upper arm. The second module is the back part which may be connected with the shoulder arrangement and which, at least partially, lies against the user's back. The third module is the pelvic support member. It may be arranged at the end of the back part that is located opposite the shoulder arrangement. The back part may introduce the force from the shoulder arrangement via the pelvic support member into the user's back and pelvis. This way, the user is able to manage heavier loads and/or work longer without damaging or putting an excessive load on his body.

The back part may be comprised of one or more parts. Preferably, the back part comprises at least one flexible-area back member that can be specifically stiffened in a bending direction by means of a stiffening device. The stiffening device may be designed so that the stiffening of the flexible-area back member is performed in a preferred bending direction; i.e., the stiffening occurs for example along the bending direction of the flexible-area back member. In other words, the user may continue to straighten up, but any further bending of the back is prevented. This way, the user may be protected against postural damage and the force that occurs in the user's shoulder can, at least partially, be transferred into the user's back and pelvis.

In a further embodiment, a flexible-area back member may comprise several stiffening means. In particular if the back part only comprises one flexible-area back member, it may be advantageous to apply a plurality of different stiffening means to it. Furthermore, one stiffening means may also be applied to the back side, i.e., facing away from the user, and one at the inside.

According to a further embodiment of the invention, a first force application point is provided on the back part on the side of the shoulder member, whereby a second force application point is provided on the back part on the side of the pelvic support member, whereby the first stiffening member is a rope that is tightened between the first force application point and the second force application point outside the bending line of the first flexible-area back member so that the bending force is specifically increased in one direction.

In a preferred embodiment of the invention, the stiffening means of the stiffening devices may be a tightened rope. This rope may be tightened between the force application points across the flexible-area back member to be stiffened. The properties of the rope such as its elasticity and the tension of the rope can be used to adjust the level of stiffness of the flexible-area back member. The rope typically runs along the outside of the back part, i.e., on the side of the back part that faces away from the user, so that the user is not in contact with the rope. The rope may also run at a distance from the flexible-area back member to provide a greater lever. Direct contact of the rope with the flexible-area back member is provided as well to achieve a low total height. The force application points may be integrated directly into the flexible-area back member, but also in other components of the back part such as the shoulder member or a connecting member.

In addition to different types and strengths of rope, the stiffening means may also consist of a spring, plastic, metal, a pneumatic cylinder, a damper, a rubber band, an electric actuator, a piezoelectric actuator, or a steel rope.

According to one embodiment of the invention, the back part furthermore comprises a second flexible-area back member with a first end and a second end as well as connecting members. The second end of the first flexible-area back member is connected with the first end of the second flexible-area back member by means of the connecting member.

For a more specific stiffening of the back part and a better adaptation to the user, the back part may comprise a plurality of flexible-area back members as well. The back part may, in particular, consist of two or three parts. The back part may, in addition to a flexible-area back member, comprise a nonflexible-area back member as well.

The stiffening of the respective flexible-area back members may be influenced by the material, the strength of the material, and the geometry of the flexible-area back member as well as by the stiffening means chosen and their connection to the back part and/or the respective flexible-area back member.

According to one embodiment of the invention, the second flexible-area back member comprises a second stiffening means with a second stiffening member, whereby the second stiffening means is designed to specifically stiffen the second flexible-area back member in a bending direction. The first stiffening means and the second stiffening means have different levels of stiffness.

For the individual adaptation of the exoskeleton to the respective user, the stiffness of the individual flexible-area back members can be adapted to the respective situation independently from each other by means of several flexible-area back members. In other words, each of the stiffening means used can stiffen the respective flexible-area back member to a different degree and the stiffening members of the stiffening means may have different tensions. The stiffening means may be modified and/or adjusted independently from each other as well.

According to one embodiment of the invention, at least one of the first flexible-area back members and the second flexible-area back member are arranged in relation to the connecting member so that their lengths can be adjusted and so that the distance between the first flexible-area back member and the second flexible-area back member is adjustable.

To adjust the exoskeleton to the respective user and his body size, the connecting member may be designed so that the distance between the flexible-area back members that are fastened to this connecting member can be changed. In other words, the connecting member may comprise a plurality of connecting points for the flexible-area back members. Hereby, a flexible-area back member may be movable or both flexible-area back members may be movably arranged. Furthermore, this functionality may be provided by the use of oval holes. Preferably, the flexible-area back member and the connecting member are connected in a detachable manner, i.e., by means of a screw.

According to one embodiment of the invention, at least one projecting retaining structure is arranged on the surface of the flexible-area back member facing away from the back part on which the stiffening member of the stiffening means rests so that the stiffening member is located at a distance from the surface of the flexible-area back member.

To produce a greater lever and therefore a greater stiffening of the flexible-area back member, the back part may have a projecting retaining structure. There may also be a plurality of retaining structures for each flexible-area back member and/or one retaining structure for each flexible-area back member. The rope may be guided over the retaining structure or through them, if they have holes. Furthermore, the retaining structure may serve to redirect the rope and therefore to achieve a more or less parallel arrangement of the rope relative to the flexible-area back member. The projecting retaining structure may be integrated directly into the flexible-area back member, but it may also be arranged on other components of the back part such as on the connecting member. A stiffening means may also be stretched across a plurality of flexible-area back members.

According to one embodiment of the invention, at least the first stiffening means comprises a rope-tensioning device that is designed to modify the rope tension.

If a higher stiffness of the flexible-area back member is desired or necessary, the tension of the rope may be increased by a rope-tensioning device. As the tension of the rope is decreased, the stiffness of the flexible-area back member is decreased as well. A separate rope-tensioning device may be provided for each stiffening means. The rope stiffening device may be adjusted manually, i.e., by the user, as well, for example by means of an adjustment screw or automatically by an actuator.

According to one embodiment of the invention, at least the first stiffening means comprises a first actuator, whereby the rope-tensioning device is designed to change the rope tension by means of the first actuator.

In addition to the manual adjustment of the rope tension by the rope-tensioning device, an automatic and/or supported adaptation of the rope tension may be performed by means of an actuator. Hereby, the actuator is integrated in the rope-tensioning device so that, when initiated and/or controlled, it can increase or decrease the tension of the rope. In another preferable embodiment, the actuator can adapt the rope-tensioning device to a given situation even while the exoskeleton is in use; i.e., the tension may be changed during a movement and/or activity of the user to adapt quickly to various situations.

According to one embodiment of the invention, the first actuator is a pneumatic cylinder, a pneumatic muscle, or an electric motor.

Depending on the area of application of the exoskeleton, the actuator may be configured in various ways for the adjustment of the rope tension; i.e., the actuator may be operated pneumatically, e.g., a pneumatic cylinder or a pneumatic muscle, electrically, piezoelectrically, or hydraulically.

According to one embodiment of the invention, the exoskeleton furthermore comprises
  a sensor arrangement to measure in particular an angle or
    a force; and
  a controller.

The controller is configured to control the first actuator of the rope-tensioning device on the basis of sensor data from the sensor arrangement so that, depending on the situation, the rope tension of the stiffening means is adjustable.

For a specific adaptation of the stiffness of the flexible-area back member, the actuator of the rope-tensioning device may be increased by one controller and one sensor. The sensor may be configured to measure a force acting on the exoskeleton, in particular a force acting on the armrest of the exoskeleton or the angle of the user's arm relative to the exoskeleton. The controller may be configured to control the actuator on the basis of the values measured by the sensor and to therefore, depending on the situation, adapt the stiffness of the flexible-area back member so that the user is assisted in his movement and/or activity to the best possible extent. This way, the user's body can be protected.

According to one embodiment of the invention, the back part and the pelvic support member are rotatably connected around a first axis of rotation, which stands orthogonally on the surface of the back part.

To ensure a lateral flexion of the user, i.e., that the user can bend sideways, the back part can be connected with the pelvic support member by means of a first axis of rotation. The first axis of rotation may stand vertically on the surface of the back part. This way, the user's freedom of motion in the exoskeleton can be increased even more.

According to one embodiment of the invention, the back part is rotatably connected with the pelvic support member by means of a second axis of rotation, which runs diagonal to the main direction of the back part in the area of the back part.

To ensure that the user can bend forward as well, a second axis of rotation can be provided in the connection between the back part and the pelvic support member. The second axis of rotation may be diagonal to the main direction of the back part.

According to one embodiment of the invention, the exoskeleton furthermore comprises a second actuator, whereby the second actuator comprises a first end and a second end. The first end of the second actuator is connected with the back part whereby the second end of the second actuator is connected with the pelvic support member, whereby the second actuator is configured to support the movement between the back and the pelvis.

For the best possible support of the user's lower lumbar spine area, a second actuator may be provided that supports the movements between the pelvic support member and the back part. Furthermore, two actuators may be arranged parallel next to the user's spine to support the lower lumbar spine area. The second actuator may be controlled by a controller as well, which controls the actuator on the basis of data measured by a sensor. The second actuator may be operated pneumatically, electrically, piezoelectrically, or hydraulically.

According to one embodiment of the invention, at least the first flexible-area back member is made from carbon-fiber-reinforced plastic.

Furthermore, the other flexible-area back members may be from carbon-fiber-reinforced plastic as well. Additionally, the flexible-area back member may be made from other materials as well such as plastic, glass-fiber-reinforced plastic, metal, textiles (mesh), or a mix of the aforementioned materials.

According to one embodiment of the invention, the exoskeleton comprises a shoulder arrangement whereby a shoulder arrangement comprises the shoulder member, a first shoulder coupling member, a second shoulder coupling member, and the armrest. The first shoulder coupling member is connected to the shoulder member by means of a first axis of rotation. The first shoulder coupling member and the second shoulder coupling member are connected with each other by means of a second axis of rotation. The second shoulder coupling member and the armrest are connected by means of a third axis of rotation. The first axis of rotation and the second axis of rotation are placed at a right angle to each other and at a distance from each other. The second axis of rotation and the third axis of rotation intersect.

The exoskeleton may comprise two shoulder arrangements as well, one for the user's left shoulder and the other for the user's right shoulder. Furthermore, an actuator may be provided between the second shoulder coupling member and the armrest which makes it possible to support the rotation around the third axis of rotation.

According to one embodiment of the invention, the shoulder arrangement furthermore comprises a translational axis along the shoulder member, whereby the first shoulder coupling member is movable along this translational axis.

To adjust the exoskeleton to the user and in particular to the user's shoulder width, a translational axis may be provided in the shoulder member. The translational axis allows for the first shoulder coupling member to be moved along the shoulder member. The translational axis may be arrested in an embodiment so that the user's shoulder width is set and then the first shoulder coupling member can no longer be moved along the translational axis. This arrest can be undone so that an adjustment to another user is possible. As an alternative, the translational axis may be configured without an arrest so that a further degree of freedom can be added to the shoulder arrangement.

According to one embodiment of the invention, the first axis of rotation is a tipping axis that is tippable at an angle between 0° and 50°.

According to one embodiment of the invention, the angle between the second axis of rotation and the third axis of rotation is between 0° and 90°, and in particular the angle between the second axis of rotation and the third axis of rotation is 85°±5°.

According to one embodiment of the invention, the exoskeleton furthermore comprises a third actuator. The third actuator comprises a first end and a second end, whereby the first end of the third actuator is connected with the armrest and whereby the second end of the third actuator is connected with the second shoulder coupling member. The third actuator is configured to support the movement of the shoulder.

The user can be supported in his movements by using a third actuator between the armrest and the second shoulder coupling member. Support can be provided in particular when performing work at or above head height or in the event of wide shoulder angles. The exoskeleton may furthermore be configured to control the stiffening of the back member depending on the support provided by the third actuator. In other words, the higher the support of the user's shoulder and/or upper arm, the more the flexible-area back member can be stiffened. In a further embodiment, the control of the first actuator, the second actuator, and the third actuator may be performed by the controller. The controller may consider data measured by the sensor or the sensors, respectively, for the control.

Furthermore, the device according to the invention may be adapted to the respective body dimensions to support the expected strain, i.e., to increase and channel force to at least one human body area, preferably an extremity. The user can put on this device or the exoskeleton, which may be made from soft or soft and hard materials. In particular the flexible-area back member is made from hard or flexible material so that it can adapt better to the user and its body. Soft components may be used in particular in areas where there is contact between the user and technology.

In connection with the invention, the term device is to be understood as a technical system with different system components such as man-technology interfaces such as, for example, an armrest or a pelvic support member (to absorb the force and therefore transfer the force from a human body part to the technical system and to transfer the force from the technical system to a human body part), connecting members, and/or devices for the realization of rotatory and/or translational movements in human body parts such as the shoulder-arm unit (also referred to as mechanics), sensors, and actuators. The device for the realization rotatory and/or translational movements must be designed in the context of this disclosure as similarly as possible to the human counterpart that is to be supported, i.e., the human shoulder; it must therefore be designed anthropomorphically. The device for the realization of human movements must be provided with a man-technology interface to absorb the force, i.e., to transfer the force from the human body part such as the upper arm to the technical system. In addition, the device must have a man-technology interface that transfers the force from the technical system back to the structures of the human body, e.g., the back, chest, and/or pelvis. This man-technology interface may, for example, be a technical device that mimics a human torso, hereinafter also referred to as the torso skeleton, which is not necessarily customized, with force induction points adapted to the user, which are individually generated by means of a 3D print. The torso skeleton may be configured differently here. A description of different variations for this is provided below. The torso skeleton can be applied for example with a bell system such as a backpack relative to the human body. Furthermore, the device for the realization of human movements comprises a drive mechanism. Various passive and active realization options exist in this regard; if active, a system of sensors and a controller may be required as well. The drive mechanism is used to generate the forces and momentums in the device that are necessary to support and mimic human movements. Passively, this could be realized in consideration of the specific properties, for example by a mechanical spring, gas-pressurized spring, or elastic bands. For an active support, electric motors, pneumatic and hydraulic actuators, or artificial muscles may be used. These active drive options have different characteristics as well. The arrangement of the drive options may be placed directly on the rotation or linear axis of the device to realize human movements. It is also possible, however, to place the drive units in a decentralized manner and to realize the actuation for example by means of a pulley mechanism.

The torso skeleton may have different configurations. What is conceivable is, for example, a purely "machine-like design" made from a system of profiles to provide purely technical functions (e.g., an easy and fast adjustment to a changed user profile). Another option would be a configuration in which the torso structure adapts to the human spine to achieve an optimal flow of force. This structure is hereinafter referred to as the S profile system as well.

The design of the arm-technology interface may differ as well. Closed and open, hard and soft structures are all conceivable.

The device is directly connected to at least two body parts of the person wearing it and interacts directly for example with the upper arm to transfer the force from the human to the technical system and to achieve the supporting function, as well as with the pelvis by means of a pelvic support member to transfer the force back from the technical system to human structures and/or the human body. The connection is preferably mechanical, which means that the user can put on the device, which is directly and closely connected with at least two specific parts of the human body. Here, the device may directly support at least one activity of the human being, predominantly lifting and handling tasks, on the one hand by transferring force around particularly used areas of the human body and on the other by providing other support and movement functions by means of a specific generation and amplification of force. This means that the system absorbs, transfers, amplifies, and introduces force and can therefore be viewed as a type of support device, for example for the upper extremities of a human being.

The support device may provide support for various movements performed by the person wearing it and is intended to avoid incorrect strain for example on human upper extremities during work performed at or above head height. The device is not, however, intended to perform all the work of the person wearing it or the user, respectively, or take over all of the strain. The system may be turned on temporarily or permanently. Furthermore, several levels of intelligence are possible. Variation one does not provide for an option to turn the system on or off. Consequently (if the user is wearing it), it is always on. Variation two allows the user to turn the system on or off (by pressing an activation button for example). Variation three provides for an integration of sensors and a controller to process the data generated by the sensors. By means of this information, strain data is used to control the system by means of EMG or force sensors depending on the level of strain. In the event of minor strain, the system is inactive, for example, and is actively added as soon as the strain surpasses a critical value.

Different scenarios are to be covered by the subject matter of the invention. These are described below in use cases.

Use case 1 provides for the use of the system to avoid excessive strain on for example the shoulder-arm area. In this case, the device is used to transfer force. Depending on the embodiment, the system is either in use permanently or temporarily. If the system has some intelligence, the system is to reduce the excessive strain for the person wearing the device in the case of excessive strain with negative effects on health (early joint wear, etc.) by the critical amount required to return to a physiologically tolerable level of strain. The objective of the system is therefore a controlled reduction of excessive strain on the person wearing the device and not a complete removal of said strain. The physiologically tolerable strain on the person wearing the device is explicitly desired due to the positive effect it has on the health of the person wearing the device (health maintenance). In general, if the device is optimally adapted to the user, the device does not constrict human movement; man and technology are synchronized in terms of time and space and perform the movement together. In the case of excessive strain, the device, which is arranged parallel to the area of the human body experiencing the strain, would specifically transfer the force. The controlling of the device during human movements and strain profile changes may take place in various ways, as described above. The composition of the device is adapted here to the person wearing it and the task to be performed.

Use case 2 provides for the use of the system only for the purpose of stabilizing and increasing force for ergonomically difficult work, such as work at or above head height, to make it possible for the user to perform the task at all. In this case the device is used primarily to generate force that is used to amplify a movement or to specifically stabilize it. Secondly, the force is to be transferred (refer to use case 1). Depending on the embodiment, the system is also active either permanently or occasionally. If the system has some intelligence, the system should only provide assistance with difficult tasks and reduce support to a minimum if support is "not absolutely necessary." The purpose of the system is therefore the controlled support of the movement of the person wearing the system. In the event of a human movement for example to rotate or lower or lift the shoulder or lift the arms, the device, which is arranged parallel to the strained region of the human being, would provide the force required for the movement (in the case of intelligent systems only as much as necessary) and, if the movement is quite small, the force required for stabilization. As described above, the device can be controlled during human movements and the strain profile changed in various ways. The configuration of the device is adapted here to the person wearing the system and the task to be performed.

The subject matter of the invention is particularly characterized by the kinematic structure of the device, which allows for human rotatory and linear movements without restriction such as rotation or the lowering and lifting of the shoulder due to the fact that the device is close to the body.

In general, the overall concept reduces the complexity, especially for the device to product rotatory and translational human movements, because movements in the vertical direction are considered which minimize the requirements placed on the actuating elements and sensors (the latter primarily for active systems) for movements in the horizontal directions.

Another special feature is the controller. Depending on the type of control that is selected, the system only becomes active if, depending on the use case, excessive strain is to be avoided or support is necessary to perform the task. One example for the avoidance of excessive strain is the manual handling of loads, when the person wearing the system either actively starts the system because he is aware of the excessive strain or if the system is configured in such a way that it automatically detects the excessive strain. The support provided for activities at or above head height is one example for the support provided in the execution of a task. The approach is equivalent to that of the first example.

Depending on the design, the device may comprise various members and different numbers of these members. The configuration, i.e., the way the members are put together to form an overall system and/or a device and the selection of the members, is made depending on the requirements that are primarily provided by the user of the system and the task. The coupling between the system and the user can be executed in various ways, for example as a backpack, carrying case, or piece of clothing. On the one hand, the system can protect body parts from excessive strain by transferring the forces acting on parts of the human body. On the other hand, the system can support and/or facilitate human movements and stabilize positions. A typical task here would be work at or above head height in the industrial production or trades. The system consists at least of a device for the realization of biomechanical and translational human movements and at least two human-technology interfaces— one to absorb force, i.e., to transfer the force from a human structure to a technical system, and one to transfer force, i.e., to transfer the force from the technical system to the human structure—as well as an actuating unit or an actuator. It is possible and sometimes even necessary in certain variations, for example those with active drive units, to add for example a sensor and control unit.

The device may be used especially to support human beings who must perform ergonomically difficult or repetitive tasks over a longer period of time. Furthermore, in the medium term, the system is intended to be used for the stabilization of at least some of the elastic or flexible technical members or technical joints or for the support of other forms of life.

The invention therefore creates a device that assists and/or preserves at least a part of the body of a human being or another living being or a technical system (such as an industrial robot) by transferring and amplifying force and that makes the performance of certain tasks possible at all.

The kinematic circumstances, in particular the anatomy of the relevant body part of the user and the task must be taken into consideration for the design, construction, and configuration of the device. Especially the two types of man-technology interfaces, the device for the realization of rotatory and translational human movements, and the actuators and maybe sensors including the controller must be considered here, which are critical for the performance of the device. These elements may be connected in a fixed or in a flexible manner so that the device may have varying degrees of freedom. All types of geometric design possibilities exist.

The subject matter of the invention only leads to minor reactive forces at the man-machine interfaces because the kinematic structure is adapted to the biomechanics of the person using the support device (leading to a high acceptance since it remains with the user). Due to its structure, the system permits a specific transfer of force into the technical system, a specific transfer of power around critical human structures, and the specific introduction of a force from the technical system to the technical system. Here, the core of this invention moves parallel to human biomechanics and is preferably designed in an anthropomorphic manner. Another design is possible as well, however. What should be particularly emphasized is a possible embodiment of the skeleton of the technical torso (referred to as the S profile system), which ensures that the system can be adapted to the physiological double-S shape of the spine, and therefore to the arrangement of the thoracic kyphosis and the lumbar lordosis.

In summary, the device is provided with one or more interfaces between the device and the user (preferably two), with one or more means for the production of rotatory and translational human movements (of the shoulder for example) and a passive and/or active drive mechanism, in the active case with a sensor device and a control unit. The device allows, on the one hand, for an ergonomically better performance of manual work, for example at or above head height, and can, on the other hand, make the performance of physically strenuous or critical tasks possible at all. The system can in particular balance out the weight of the objects held by the user by providing support to the upper extremities. Due to the specific arrangement of actively driven and passive degrees of freedom of at least a part of the device for the production of rotatory and translational human movements, it is possible in a conceivable embodiment to transfer vertically acting forces in particular from the upper extremities to the torso, whereas the user is only somewhat limited in the horizontal direction. It is therefore possible to constructively separate the harmful strain caused by weight from movements on the horizontal level, which are useful for health reasons and important for the handling.

These types of systems make it possible to involve employees in various application contexts in their field of work because early wear and tear can be reduced and because these systems can counteract a decrease in physical performance. The system can be used both in the professional sector, for example for lifting and carrying tasks, and in the private arena, for example for the installation of lamps or when painting.

The subject matter of the invention is a portable, in particular wearable, system to avoid damage caused by excessive strain and to provide support for ergonomically difficult activities. Different variations are conceivable for the specific design of the system. The mobility of the user, i.e., the human movement, is generally not influenced or impaired. Various types of materials, which can be soft or hard, such as aluminum, textiles, GRP, CFP, or plastic may be used for the structure of the system.

In summary, the subject matter of the invention is characterized especially by the following aspects:

The specific coupling of rotatory and translational degrees of freedom in a kinematic structure leads to a very high fidelity of movement of the support system.

Another significant advantage of the device is the much easier, more compact, and more cost-effective design.

Special measures (in particular from biomechanical analyses) were taken into consideration for the configuration of the kinematics to produce an anthropomorphous design for the system that is positioned close to or worn on the body. This causes the fidelity of movement to be very well reproduced in spite of the reduction of the degrees of freedom.

The modular structure and specifically provided adaptation options facilitate an optimum use of the device according to the invention.

Negligible constraining forces (meaning that the choice to use the system rests with the user) due to the kinematic structure and/or actuating elements, which primarily compensate for the force of weight as well as the very good adaptation options and the design of the system, which is very close to the body and compact, lead to high acceptance.

BRIEF DESCRIPTION OF THE FIGURES

Exemplary embodiments of the invention are shown in the drawings and are described in further detail below.

DESCRIPTION OF EMBODIMENTS OF THE INVENTION

A preferred area of application of the support device according to the invention is the support of physically working people in the private and professional environment at ergonomically critical tasks such as work performed at or above head height such as installation and assembly tasks performed by technicians in the automotive and aerospace industry. These are all tasks that are currently and will in the future still be preferably performed by human beings. The demand for this is constantly increasing due to demographic changes and the increased requirements in the production environment due to more complex and more customized products. The support device according to the invention ensures that the work can be performed for a longer period of time than previously due to the specific relief and assistance it provides, thereby reducing damage caused by excessive strain over a longer period of time. It also makes certain work that requires special skills possible at all (the handling of heavy loads, for example). Furthermore, it can make work easier for groups of persons who were previously not optimally equipped for this type of work. These application examples show that the issue is of significant social relevance (sustained use of human resources in the private and professional environment). The gap of a necessary system technology for a targeted support can be reduced by the support device without replacing the human being with a technical system. Consequently, the economy as a whole can be strengthened because sick days per employee can be reduced due to the avoidance of incorrect strain.

The subject matter of the invention supports the user with a wearable support device which comprises elements that are arranged parallel to at least one human body part and that can be controlled in various ways and that, in total, constitute a support device. This may include functions for regulating and controlling the device elements and any required sensors as well.

Below, embodiments will be illustrated on the basis of a use case, work at and above head height, of the device according to the invention.

Figure 1:
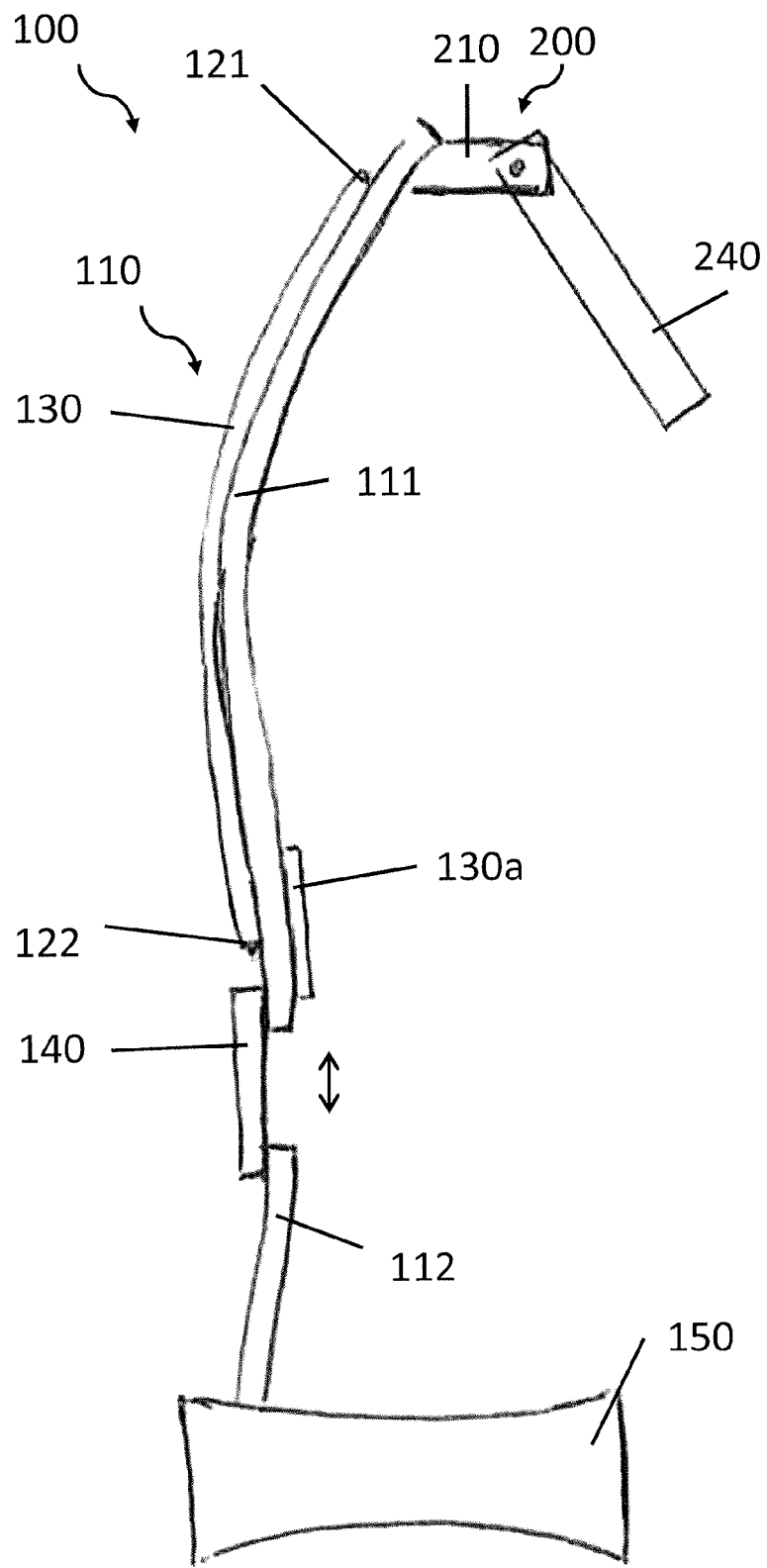
FIG. 1 shows a schematic view of an exoskeleton from the side according to an embodiment of the invention.

FIG. 1 shows an exoskeleton from a side view. The exoskeleton 100 in FIG. 1 comprises several modules including the back part 110, the shoulder arrangement 200, and the pelvic support member 150. The back part 110 connects here the pelvic support member 150 with the shoulder arrangement 200. The shoulder arrangement 200 comprises at least one armrest 240 and one shoulder member 210. The back part 110 comprises at least a first flexible-area back member 111. It is flexibly designed vertical to the main extension direction so that a user can bend the first flexible-area back member 111. The first flexible-area back member 111 is directly or indirectly connected with the pelvis support member 150 and connected with the shoulder arrangement 200. In the case of an indirect connection between the first flexible-area back member 111 and the pelvic support member 150, a second flexible-area back member 112 and/or a connecting member 140 may produce the connection between the first flexible-area back member 111 and the pelvic support member 150, whereby the distance between the first flexible-area back member 111 and the second flexible-area back member 112 is adjustable by means of the connecting member 140. Therefore, the exoskeleton 100 can be adapted to users with different body shapes. A first stiffening means 130 may be applied to the first flexible-area back member 111, which makes it possible to specifically stiffen the flexible-area back member 111 in a bending direction. The first stiffening means 130 can be applied outside relative to the back of the user on the first flexible-area back member 111. The first stiffening means 130 is connected with the first flexible-area back member 111 by means of two force application points 121, 122. The first force application point 121 is here arranged on the side of the shoulder arrangement and the second force application point 122 on the side of the pelvic support member.

An inner stiffening means 130a is applied on the inside of the flexible-area back member 111 in FIG. 1 as well so that the second bending direction can be specifically stiffened as well. Furthermore, the areas of the first stiffening means 130 and of the inner stiffening means 130a may overlap so that the first flexible-area back member is stiffened both in the first and in the second bending direction.

Figure 2:
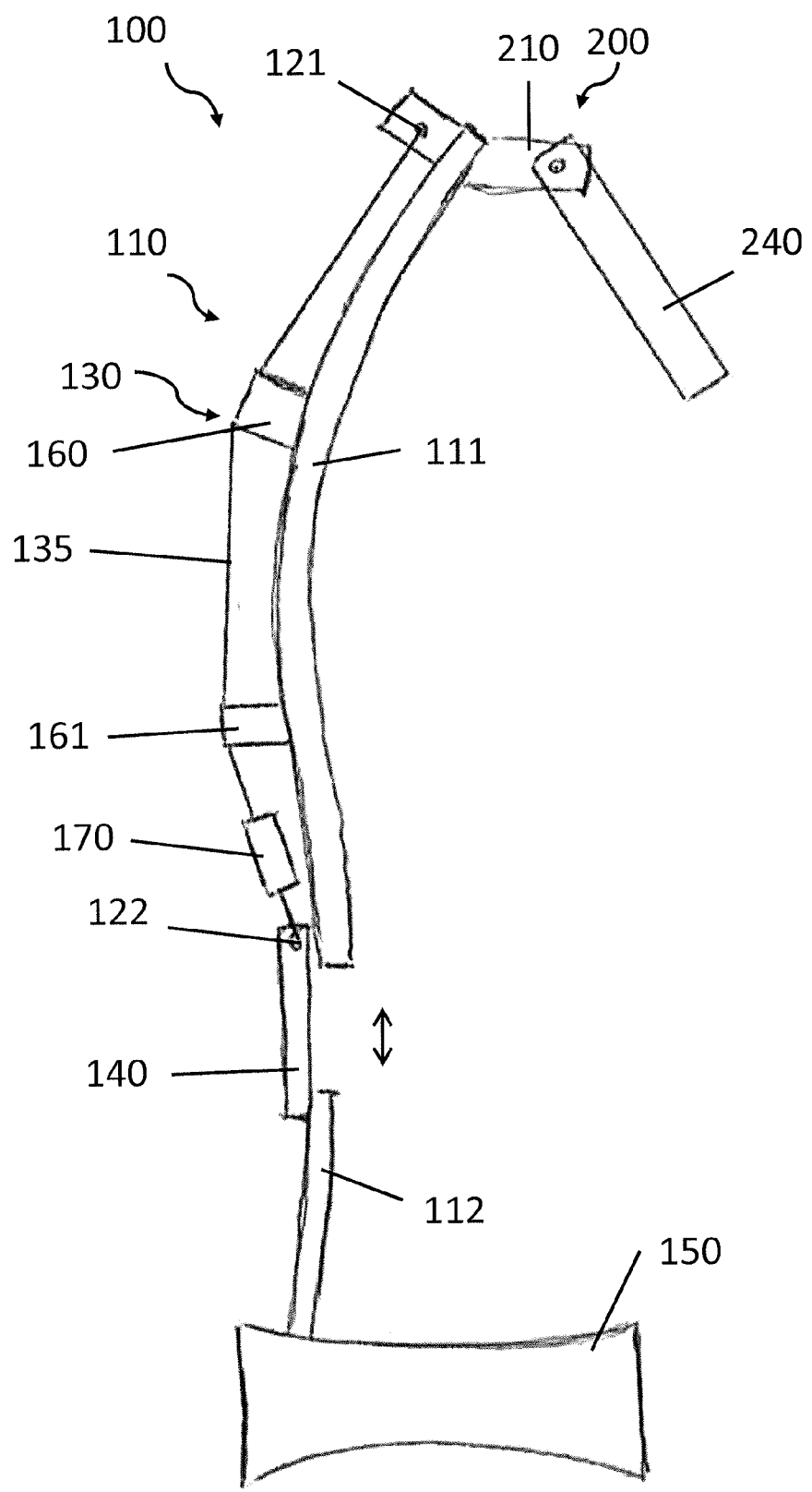
FIG. 2 shows a schematic view of an exoskeleton with a spaced-apart stiffening means from the side according to an embodiment of the invention.

FIG. 2 essentially shows the exoskeleton 200 from FIG. 1. In FIG. 2, the exoskeleton disposes of a shoulder arrangement 200 with an armrest 240 and a shoulder member 210 as well. Furthermore, the exoskeleton 100 comprises a back part 110 and a pelvic support member 150, whereby the back part 110 connects the pelvic support member 150 with the shoulder arrangement 200. Differently from FIG. 1, FIG. 2 has a different type of stiffening device 130. The stiffening device 130 furthermore comprises stiffening means 135, whereby this is arranged in FIG. 2 between the first force application point 121 and a second force application point 122. The first force application point 121 is located on the shoulder member 210. The second force application point 122 is located on the connecting member 140. Furthermore, protruding retaining structures 160, 161 are fastened on the first flexible-area back member 111 on which the stiffening means 135 has been placed. The stiffening means 135 can be a tight rope or a spring, for example. Due to the retaining structures 160, 166, the distance between the stiffening means 135 and the first flexible-area back member 111 to be stiffened can be adjusted so that a more specific stiffening of the first flexible-area can be ensured. Furthermore, the stiffening device 130 comprises a rope-tensioning device 170. This rope-tensioning device 170 makes it possible to adjust the rope tension and/or the spring tension. The adjustment can be made manually or automatically. The rope tension can preferably be adjusted to the needs of the user, e.g., his body size, muscle strength, and the work to be performed. For an automatic adjustment of the rope tension, an actuator may be provided in the rope-tensioning device 170. This may be for example a pneumatic cylinder, a hydraulic cylinder, a pneumatic muscle, a piezoelectric element, or an electric motor. Furthermore, it is possible to use a controller and a sensor arrangement for the control of the actuator. This way, the actuator can be adapted to the respective situation; i.e., depending on the forces that are in play and/or the angles of the exoskeleton 100, the stiffening of the stiffening device 130 can be adapted. Consequently, the stiffness of the back part 110 can be adapted and the user individually supported.

Figure 3:
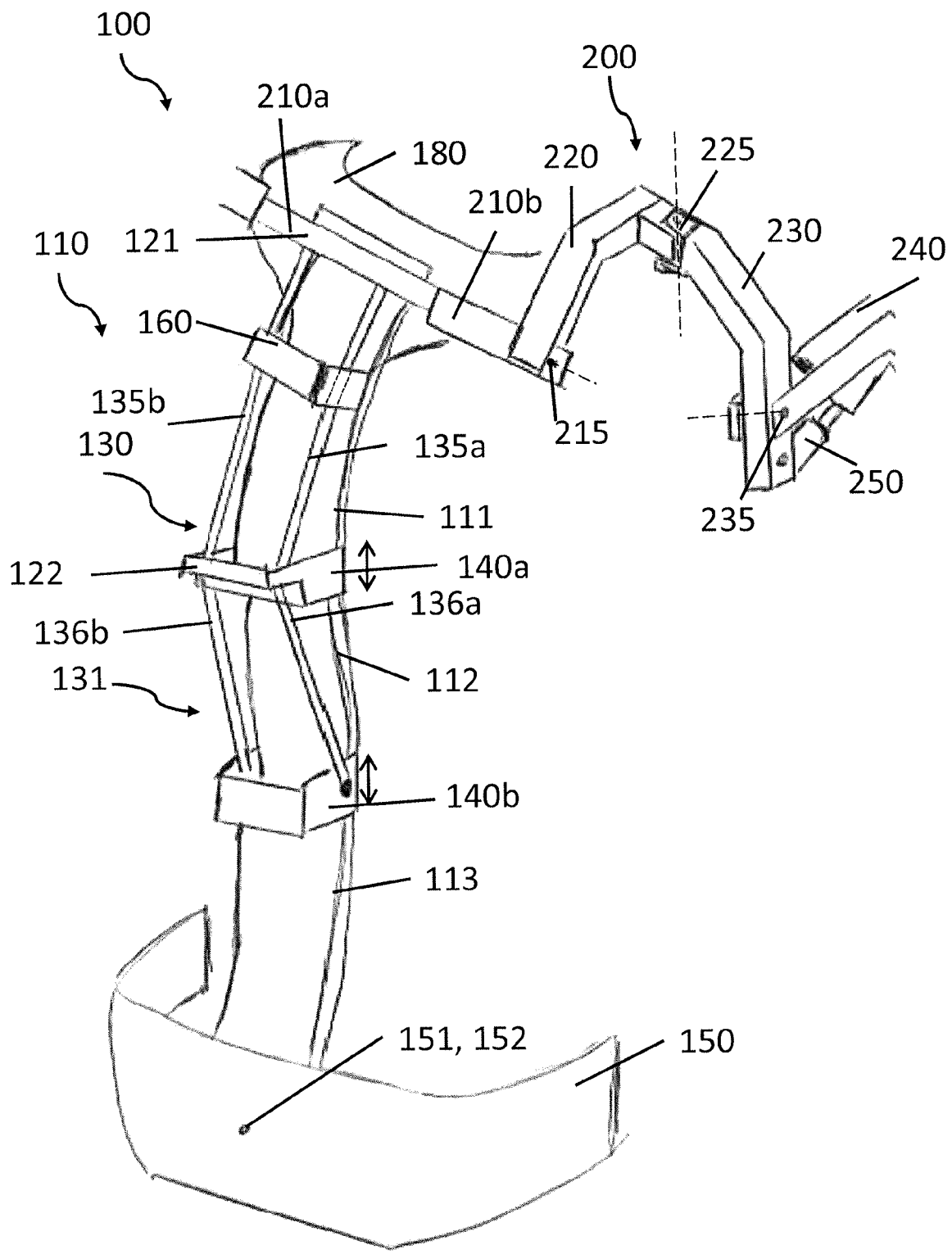
FIG. 3 shows a schematic view of an exoskeleton with a spaced-apart stiffening means from an isometric perspective according to another embodiment of the invention.
Figure 4:
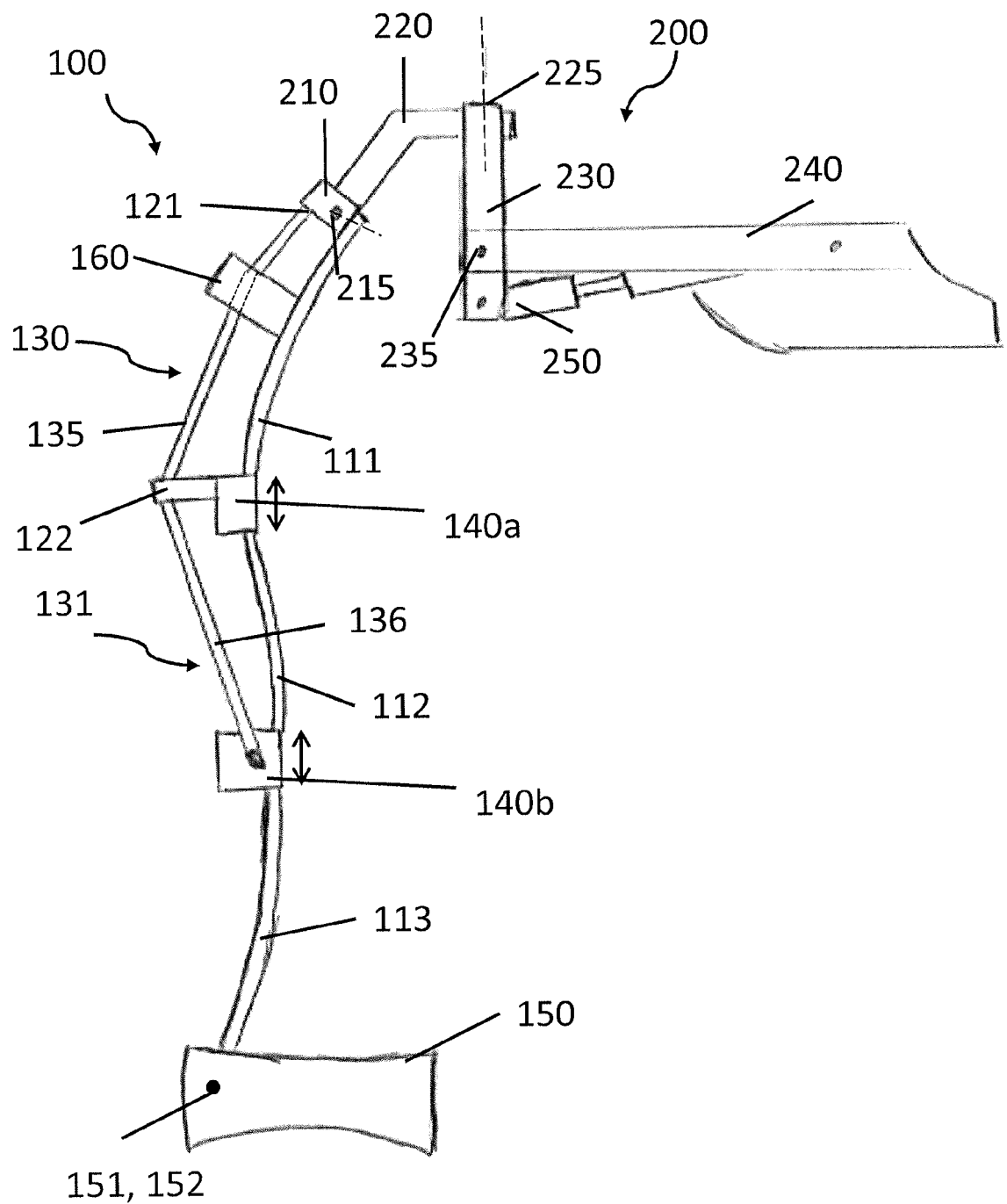
FIG. 4 shows a schematic view of an exoskeleton with a spaced-apart stiffening means from the side according to another embodiment of the invention.

FIG. 3 and FIG. 4 show an exoskeleton 100 according to an embodiment of the invention in an isometric or a lateral view, respectively. Contrary to FIGS. 1 and 2, the back part 110 in FIG. 3 has three parts; i.e., there are three flexible-area back members 111, 112, 113 which are connected by means of two connecting members 140a, 140b. The connecting members 140a, 140b make it possible to change the distance between the connected flexible-area back members so that the height can be adjusted to that of the respective user. Furthermore, FIG. 3 has a shoulder pad 180 which is used to comfortably position the exoskeleton on the user's shoulders. The connection between the third flexible-area back member 113 and the pelvic support member 150 is created by means of an arrangement comprising a first axis of rotation 151 and a second axis of rotation 152. The first axis of rotation 151 allows the user to bend his back sideways, i.e., to perform a lateral flexion of the back. The second axis of rotation 152 allows the user to bend forward, i.e., a bending of the pelvic support member 150 relative to the third flexible-area back member 113. In FIG. 3, the first stiffening device 130 has two parallel stiffening means 135a, 135b which are suspended above the first flexible-area back member 111. In this case, the stiffening means 135a, 135b are tight ropes. A first force application point 121 is located, as in FIG. 2, at the shoulder member 210. The second force application point 122 of the first stiffening device 130 is located on the stiffening means 140a. The stiffening means 135a, 135b pass through the retaining structure 160 to create a connection between the first force application point 121 and the second force application point 122. Furthermore, the retaining structure 160 creates a distance between the stiffening means 135a, 135b of the first flexible-area back member 111. Due to this arrangement, the first stiffening device 130 can specifically stiffen the first flexible-area back member 111. A second stiffening device 131 is arranged above the second flexible-area back member 112. The second stiffening device 131 comprises two parallel stiffening means 136a, 136b as well. The stiffening means 136a, 136b are strung between the two connecting members 140a, 140b and are designed to specifically stiffen the second flexible area back member 112. The rope tension of the various stiffening means 135a, 135b, 136a, 136b may be designed differently, but also similarly. Furthermore, FIG. 3 comprises a shoulder arrangement 200, which is described in further detail in FIG. 5-7.

Figure 5:
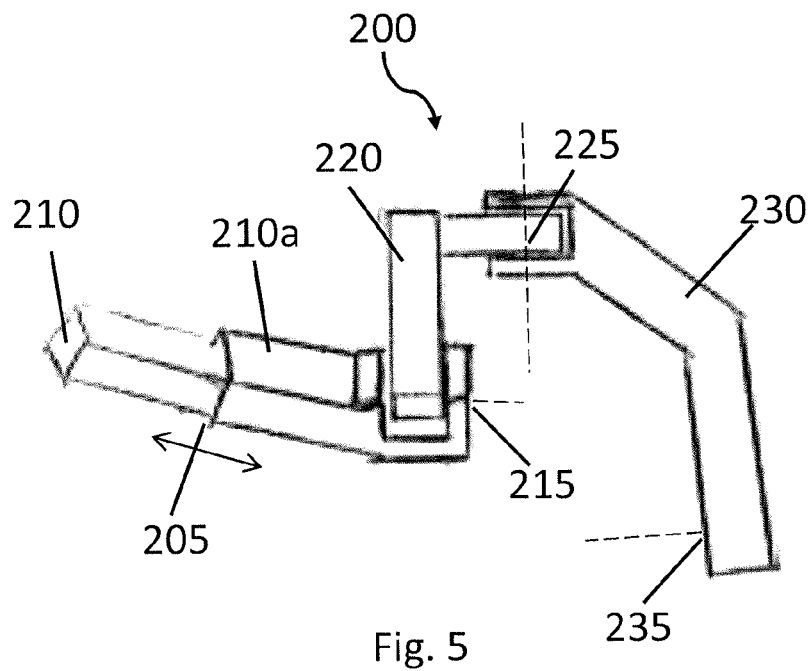
FIG. 5 shows a shoulder arrangement according to an embodiment of the invention.
Figure 6:
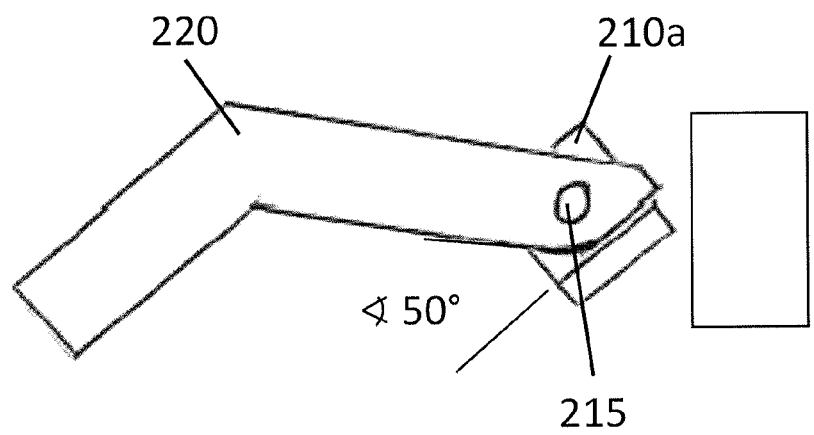
FIG. 6 shows the first axis of rotation, which is a tilting axis, according to an embodiment of the invention.
Figure 7:
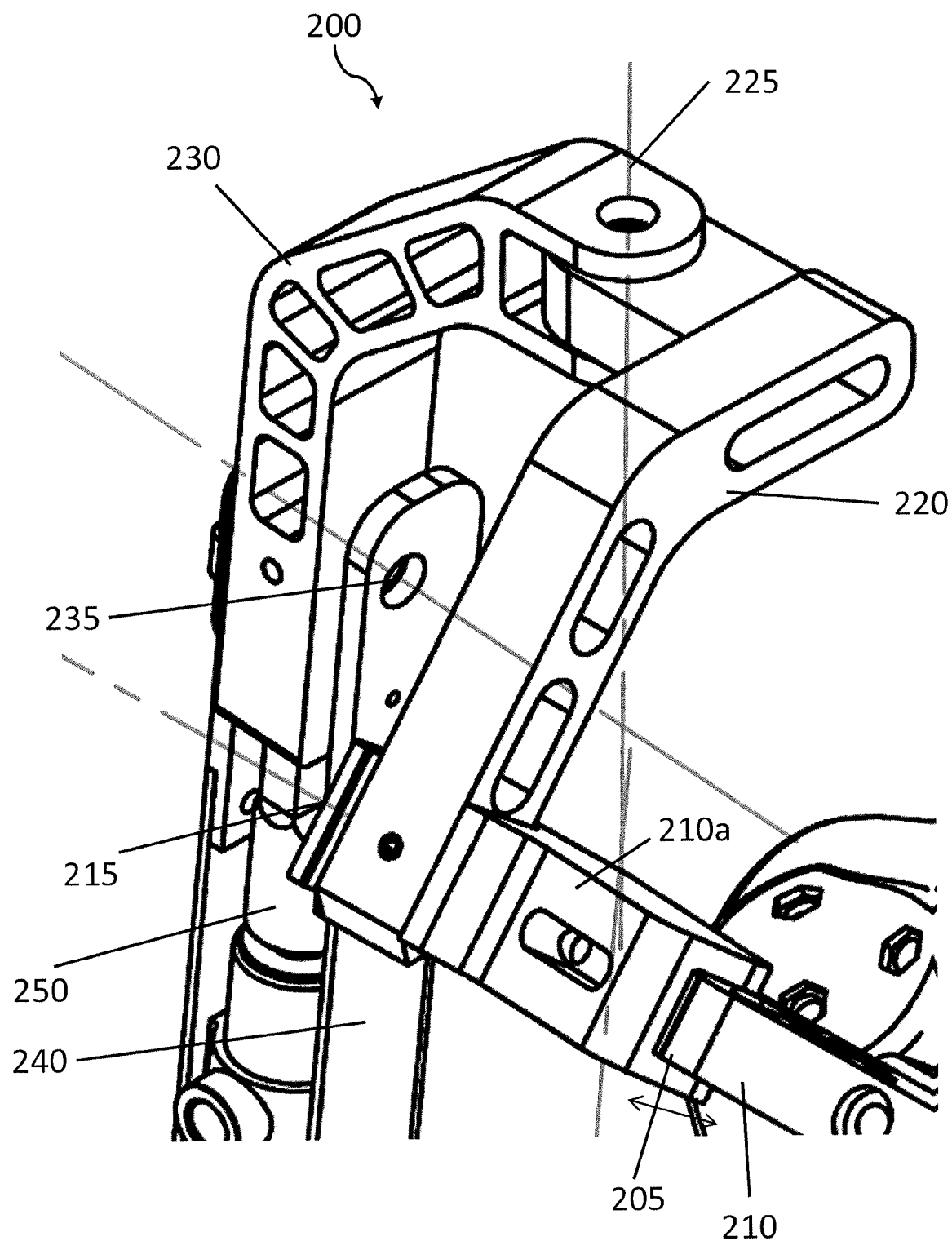
FIG. 7 shows a shoulder arrangement in an isometric view according to an embodiment of the invention.

FIG. 5 and FIG. 7 show a shoulder arrangement 200. The shoulder arrangement 200 comprises the following components: a shoulder member 210, 210a, a first shoulder coupling member 220, a second shoulder coupling member 230, and an armrest 240. The shoulder member 210 may be two-part so that it comprises a first part 210 and a second part 210a. This way, a translational axis 205 can be provided, since the one part can be inserted into the other part to adjust the exoskeleton to the user's shoulder width. The translational axis 205 can be arrested in one embodiment after it has been set so that it does not move during use and so that the force can be effectively transferred to the back part and the pelvic support member. The shoulder member 210 or 210a is connected to the first shoulder coupling member 220 in a rotatory manner so that a first axis of rotation 215 is created. The first axis of rotation 215 can be designed as a tilting axis, which is described in further detail in FIG. 6. The first shoulder coupling member 220 is connected with the second shoulder coupling member 230 by means of a second axis of rotation 225. The second shoulder coupling member 230 is connected with the armrest 240 by means of a third axis of rotation 235. The second axis of rotation 225 and the third axis of rotation 235 intersect at an angle between 0° and 90°, in particular at an angle of 85°±5°. The second axis of rotation 225 and the first axis of rotation 215 do not intersect directly because the first shoulder coupling member 220 protrudes both laterally and toward the back. Therefore, these two axes of rotation are orthogonal to each other but at a distance from each other. The shoulder arrangement 200 described above with a total of three axes of rotation 215, 225, 235 allows for a high degree of mobility in the user's shoulder area. An actuator 250 may be arranged between the armrest 240 and the second shoulder coupling member 230. It may be designed to support the user's arm. As a result, the user can perform longer work with tools and/or work better about head height. Furthermore, a sensor may measure the force or the angle for the controlling of the actuator 250 to provide ideal user support.

FIG. 6 shows a section view of the first axis of rotation 215. Furthermore, FIG. 6 shows the first shoulder coupling member 220 and the shoulder member 210a. The first axis of rotation 215 is a tilting axis, which is tiltable at an angle of 50°. The design provides that the desired angle, here 50°, can be set by means of two stops. This way, any excessive stretching of the human being is prevented.

FIGS. 8 to 11 each show a possible embodiment of the support device or the exoskeleton for the application context of work at and above head height. This application is an ergonomically very critical use case. The application is to help employees, especially those in production, avoid chronic damage in their shoulder area (use case 1 force transfer) or even make it possible to perform work at and above head height (use case 2 force increase).

Figure 8:
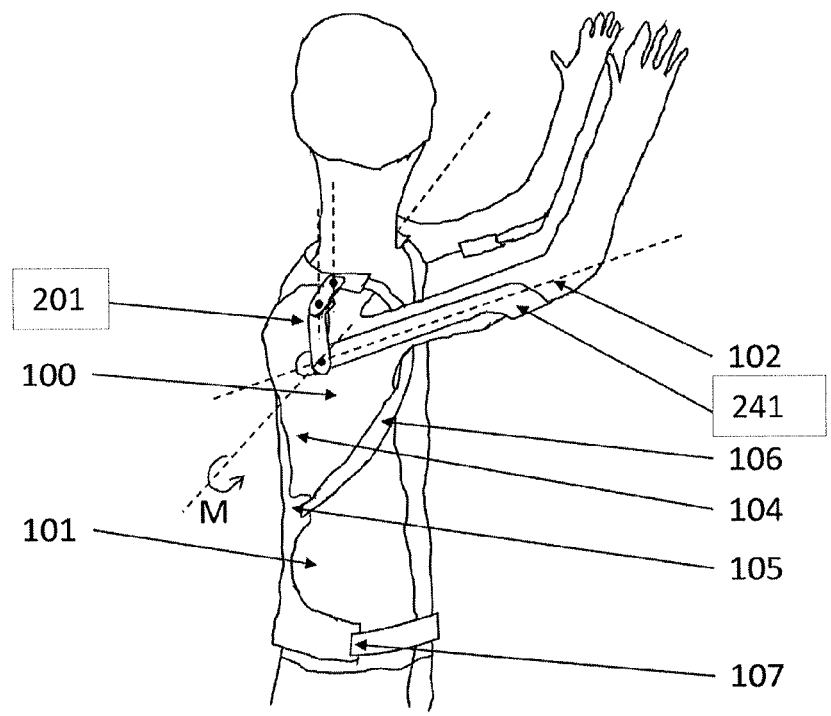
FIG. 8 shows a first example of a support device according to the invention, its interaction with a person when performing a task either at or above head height from a side view of the body

FIG. 8 outlines a first example for a support device 100 whose interaction with the user 101 and between the system elements is shown. The support device 100 is coupled with the user 101 by means of two man-technology interfaces: one interface between the support device 100 and the upper arm of the user 102, for example an armrest, identified as the interface between the technical system and the human arm (arm-system interface 241) and one interface between the support device 100 and the human torso 104, identified as the interface between the technical system and the human torso (system-torso interface 105), for example a pelvic support member. The system-torso interface 105 is equipped with a wearer/connection system 106. Furthermore, the system-torso interface 105 has a connection point with the human pelvis 107 which must be especially adapted to the user 101. Furthermore, the support device 100 has a device to produce especially rotatory human movements 201, which is arranged between the system-torso interface 105 and the arm-system interface 241. This possible configuration of the device for the production of human movements 241 has three degrees of freedom. An actuator unit or an actuator is not shown in FIG. 8 but may still be required. Possible embodiments for the actuator unit and furthermore for the sensors and controller that are required for active actuator units are shown above.

Figure 9:
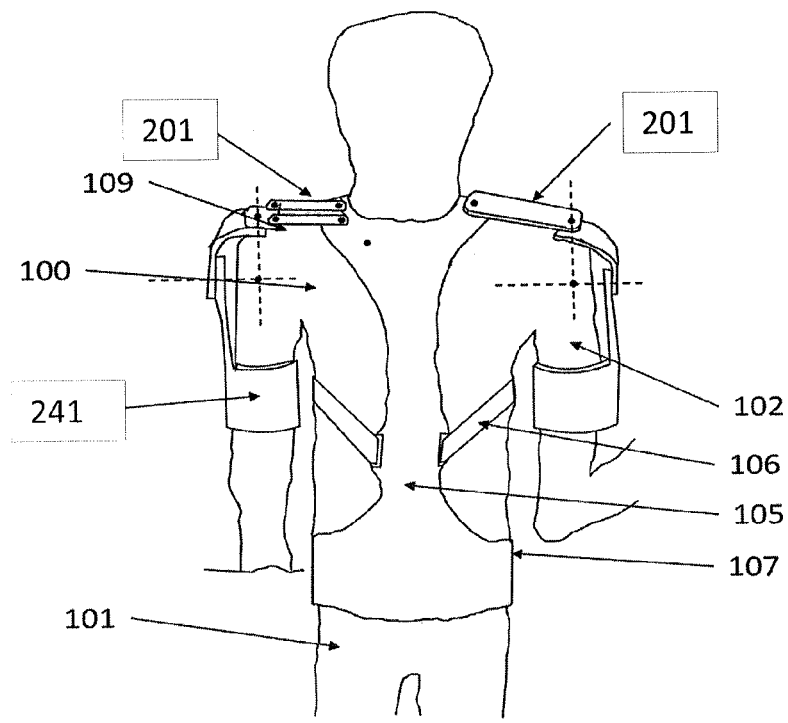
FIG. 9 shows a first example of a support device according to the invention, its interaction with a person when in rest showing the back of the body

FIG. 9 shows a second drawing of another embodiment of the supporting device 100 according to the invention with an especially different configuration of the device for the production of rotatory and translational human movements 201, whereby the configuration from FIG. 8 is shown on the right and the new variation on the left. The embodiment on the left, partially parallel kinematics, also allows for the production of the rotatory human movement in addition to the production of translational human movement. This special part of the kinematics of the device is arranged above the human shoulder 109.

Figure 10:
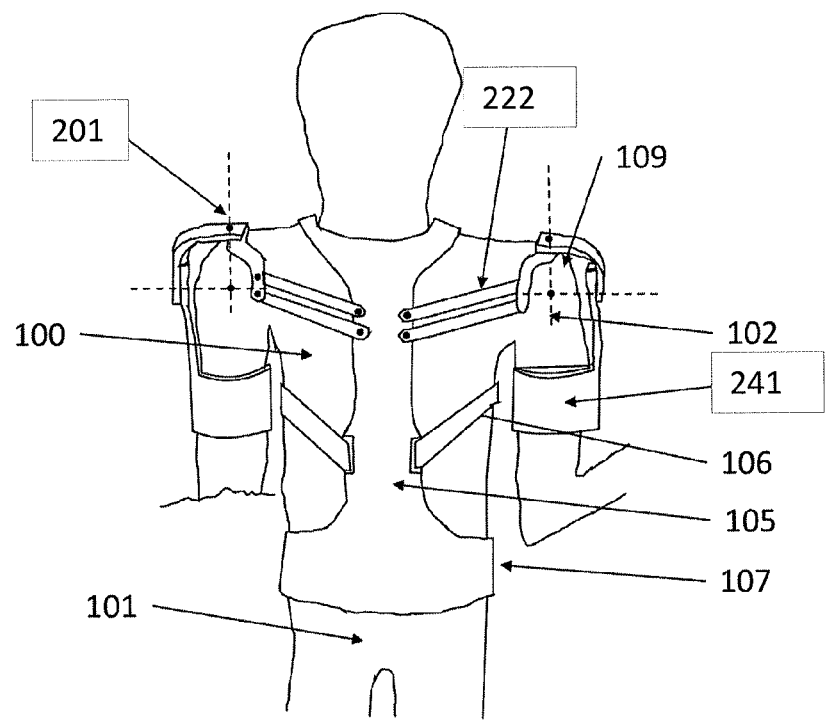
FIG. 10 shows a second example of a support device according to the invention, its interaction with a person when in rest showing the back of the body

Another embodiment of the support device 100 is shown in FIG. 10. The main difference here is in the device for the production of rotatory and translational human movements 201. The configuration of this device is, compared to the embodiments from FIG. 8 and FIG. 9, fundamentally different to improve the fidelity of movement. A parallel kinematics 222 arranged at the top back of the user represents the function "lift/pull up the shoulders" (two-dimensional movement) in the device for the production of human movement.

Figure 11:
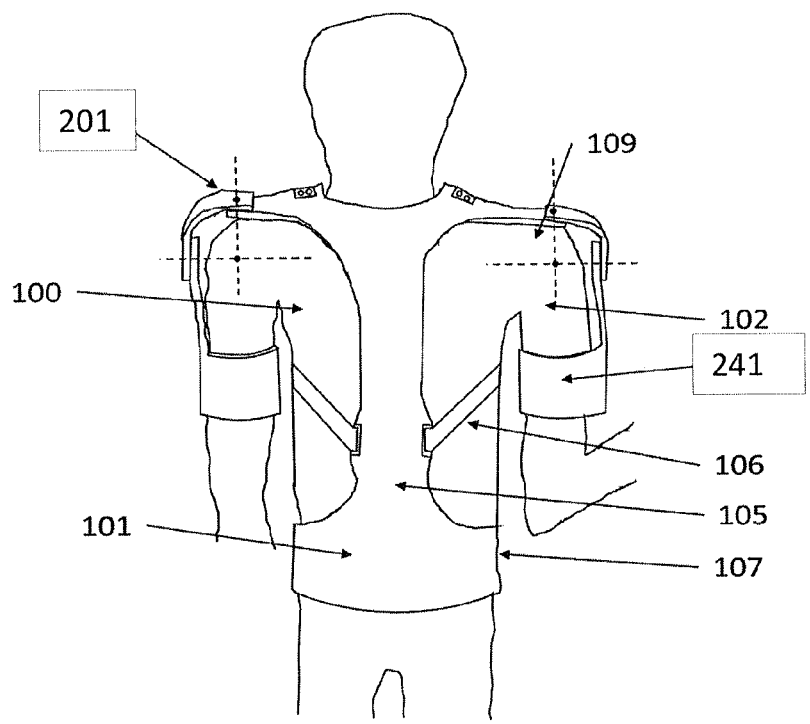
FIG. 11 shows a third example of a support device according to the invention, its interaction with a person when in rest showing the back of the body

A fourth embodiment for the device for the production of human movements 201 is outlined in FIG. 11. This embodiment has two degrees of freedom, especially for the production of rotatory human movements. Due to the different design of the device for the production of human movements 211, a differently designed system-torso interface 105 is required, especially above the human shoulder 109.

All four roughly sketched supporting devices or exoskeletons 100 support at least one arm (specifically the upper arm 102) of the user 101 who, in the drawings, is coupled directly with the supporting device 100 by means of an interface. Different variations for the device for the production of rotatory and translational human movements 211 have been outlined. The variations and embodiments for the integration and configuration of the actuating unit and, in the case of active systems, of the sensor and control unit were not shown. The embodiments were described above.

Figure 12:
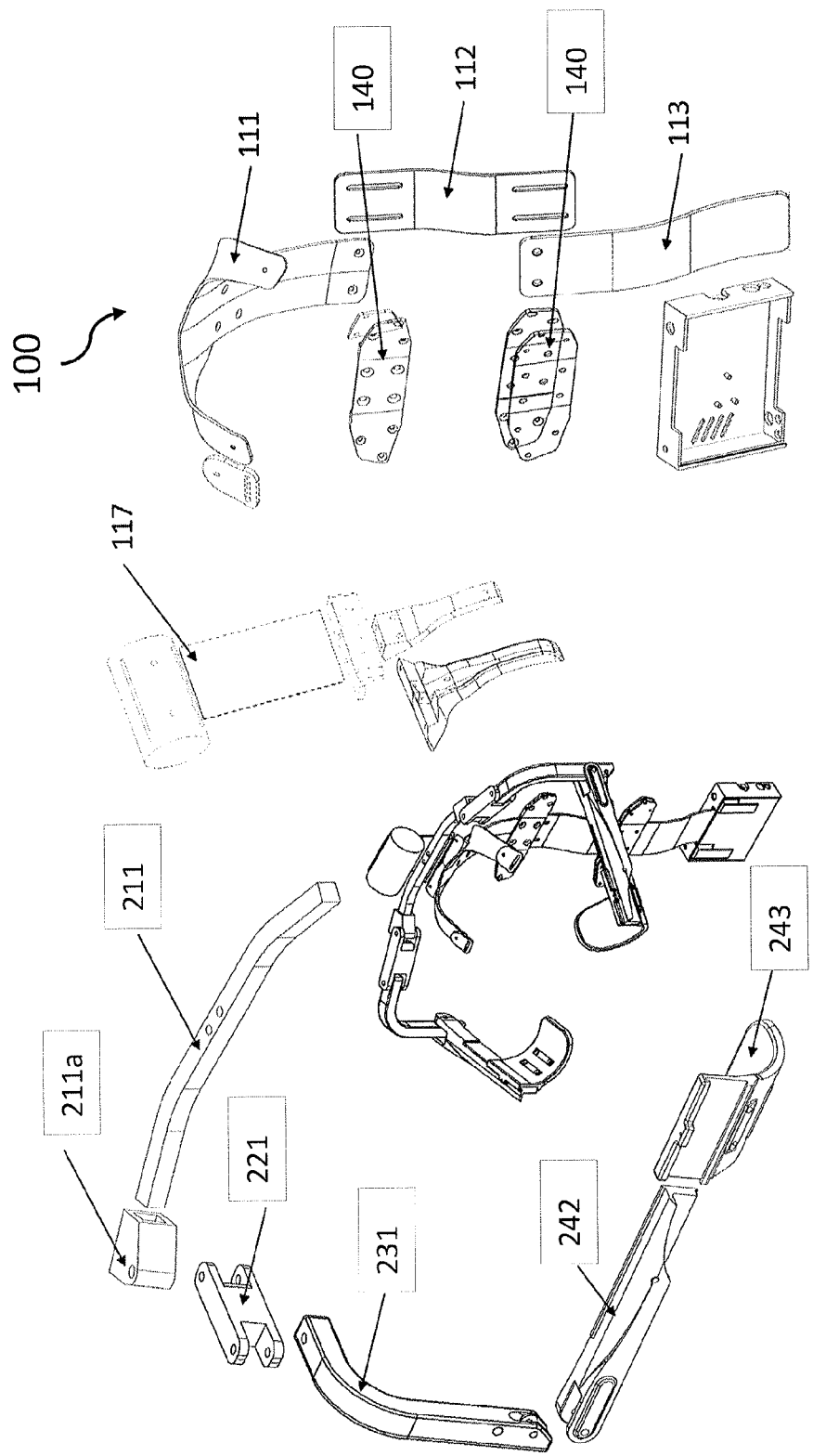
FIG. 12 shows an exploded view of the device according to the invention according to an embodiment of the invention.

Another option is shown in FIG. 12. The configuration of the back or the back part is different here. It consists of an upper back member 111, a middle back member 112, and a bottom back member 113. What is special about this is that this design provides for adjustment options that make it possible to adjust to the height of every user. The back has an S-shaped profile (to reflect the spine). The back members can be made from different materials such as plastic, carbon-fiber-reinforced plastic, glass-fiber-reinforced plastic, or metal. Especially carbon-fiber-reinforced plastic is considered suitable in this regard, however, because this material adapts more easily to directional stiffness properties. In that case, it is possible to build a structure that is so soft that it allows the back to bend but is still able to transfer the forces that arise. The top back member 111 just barely covers the shoulders. No further coverage is required because no forces are to be absorbed and/or transferred here. In this area, only a referencing and arresting has to be possible. The back members are connected for example by means of screws.

In addition, the back system is provided with a backpack holder. Special elements 140 are provided for the one connection side. Another connecting member is required for a chest restraint, which comprises the user's chest strap, but here as well only for referencing and arresting purposes, not for the transfer of force. The bottom back member 113 is, in turn, connected with a pelvic strap (not shown). At the top back member 111, a connecting member 140 is attached which allows for a connection with the other system parts. These include on the one hand the arm kinematics and the headrest 117 on the other. The underlying connection with the arm kinematics is provided by a deflection bow 118 which is connected with the connecting member 140. One or two arm members may be attached to this deflection bow. These arm members consist of four mechanical elements, a man-technology interface, and an actuator (not shown). The four elements include the arm-deflection bow connection 211a, a fork bridge 221, a 90° deflection bow 231, and the arm lever 242. The actuator is braced between the arm lever 242 and the 90° deflection bow 231. A gas-pressurized spring, a pneumatic actuator, or an electric motor may be used as an actuator. Furthermore, sensors can be integrated for calculation of the target value. The man-technology interface 243 is installed on the arm lever 242. The position may be determined by a control.

For the context in which the supporting devices shown in FIGS. 8-11 can be used, it is important that the user does not have to bear the weight of his own extremities and that of the tools held. Especially in static situations, the human muscles are limited in their performance when it comes to dynamic strain due to the decreased blood circulation. It is, however, generally not necessary to support the user in the positioning or to increase the dynamics in the horizontal direction. Therefore, the construction and design in the concept described here specifically supports in the vertical direction, whereas as little force as possible is transferred to the user in the horizontal direction. This is achieved due to the fact that passively designed axes of rotation run parallel to the gravitational direction. Actively or passively driven axes of rotation run parallel to the floor. The torque at the axis of rotation is selected depending on the angle between the longitudinal axis of the body and the longitudinal axis of the mechanical structure that runs parallel to the supported body part in such a way that the highest torque is reached at the point of the greatest lever arm. For a supporting system attached to the upper arm, this principle leads to a driving torque of $$M_{Drive} = \sin(\phi_{Upperarm}) * M_{Drive,maximum}$$

from a preset maximum support torque $M_{Drive,maximum}$ with an angle $\phi_{Upperarm}$ between the body's longitudinal axis and the upper arm. In addition to the angle $\phi_{Upperarm}$, further physiological parameters such as the course of the maximum muscle force above the joint angle (course of the muscle strength) can be included in the calculation to ensure that the supporting force is less than the force required for the performance of the work. This means that the system does not move the user. The user must always apply force. For other body joints, identical relationships can be created between the joint angle and the supporting force. A suitable combination makes it possible to ensure that some of the harmful strain caused by the weight is removed from the user, while his freedom of motion remains intact.

Especially for translational movements such as those that occur on the shoulder strap, other movement patterns are conceivable as well. For physiological reasons, it makes sense here to turn on the force counteracting gravitation when an angle of 90° between the upper arm and the longitudinal axis of the body is exceeded.

Further sensors (such as EMG sensors) can be integrated to detect the user's intention. The concept of the special compensation of gravitational influence is maintained and expanded by a situational influencing of the maximum supporting force $M_{Drive,maximum}$.

The design construction described makes it possible to store the potential energy in a simplified manner (for example as elastic energy in springs or pressurized air) and to return it to the user as needed.

In addition to this fixed-body consideration, it is also important to note that the supporting device consists of flexible elements (especially in the back area). These are applied in such a way that they are stiff relative to the direction of the main supporting force, but flexible in the other direction. This way, they can adapt to the form of the body and the movement (especially the flexion of the back, refer to the system-torso interface 105 in FIG. 1). Overall, this is achieved by using flat structures close to the body. By using textile fasteners (cf. wearer/connecting system 106 in FIG. 9) around the respective body part, the structure adapts to the body part and does not break off when strain is applied parallel to the longitudinal axis.

REFERENCE NUMBER LIST

100 Exoskeleton or supporting device
101 User
102 User's upper arm
104 Human torso
105 System-torso interface
106 Wearer/connecting system
107 Human pelvis
109 Human shoulder
110 Back part
111 First back member
112 Second back member
113 Third back member
114 Connecting member for backpack holder
116 Joining member
117 Headrest
121 First force application point
122 Second force application point
130 First stiffening device
131 Second stiffening device
135 First stiffening member (a, b)
136 Second stiffening member (a, b)
140 Connecting member
150 Pelvic support member
151 First point of rotation of the pelvic support member
152 Second point of rotation of the pelvic support member
160 Retaining structure
161 Retaining structure
170 Rope-tensioning device
180 Shoulder pad
200 Shoulder arrangement
201 Device for the production of human movements
205 Translational axis
210 Shoulder member
211 Bow connection
211a Arm-deflection bow connection
215 First axis of rotation
220 First shoulder coupling member
221 Fork bridge
222 Parallel kinematics of an embodiment of the device for the production of human movements
225 Second axis of rotation
230 Second shoulder coupling member
231 90° bow connection
235 Third axis of rotation
240 Armrest
242 Arm lever
243 Man-technology interface
250 Arm supporter (actuator)

The invention claimed is:
1. An exoskeleton for a human being, comprising:
a shoulder member;
at least one armrest;
a pelvic support member;
a back part with a first end and a second end;
whereby the back part comprises at least a first flexible-area back member with a first and a second end and at least a first stiffening device with a first stiffening means,
whereby the first flexible-area back member is oriented so that its first end faces the first end of the back part and its second end faces the second end of the back part,
whereby the first end of the back part is attached to the shoulder member,
whereby the second end of the back part is attached to the pelvic support member,
whereby the armrest is directly or indirectly articulated to the shoulder member,
whereby the first stiffening means is designed so that the first flexible-area back member is specifically stiffened in a bending direction, and
whereby at least one protruding retaining structure is arranged on the surface of the flexible-back member facing away from the back part, on which the stiffening means of the stiffening device rests, so that the stiffening means is located at a distance from the surface of the flexible-area back member.

2. The exoskeleton according to claim 1,
whereby a first force application point is provided on the back part at the side of the shoulder member,
whereby a second force application point is provided on the back part at the side of the pelvic support member,
whereby the first stiffening means is a rope that is tightened between the first force application point and the second force application point outside the bending line of the first flexible-area back member so that the bending force is specifically increased in one direction.

3. The exoskeleton according to claim 1,
whereby the back part furthermore comprises a second flexible area back member with a first end and a second end as well as a connecting member,
whereby the second end of the first flexible-area back member is connected with the first end of the second flexible-area back member by means of the connecting member.

4. The exoskeleton according to claim 3,
whereby the second flexible-area back member comprises a second stiffening device with a second stiffening means,
whereby the second stiffening device is configured to stiffen the second flexible-area back member specifically in a bending direction,
whereby the first stiffening device and the second stiffening device have different levels of stiffness.

5. The exoskeleton according to claim 3,
whereby at least one of the first flexible-area back member and the second flexible-area back member is arranged relative to the connecting member so that its length can be adjusted and so that the distance between the first flexible-area back member and the second flexible-area back member can be changed.

6. The exoskeleton according to claim 2,
whereby at least the first stiffening device comprises a rope-tensioning device which is designed to change the rope tension.

7. The exoskeleton according to claim 6,
whereby at least the first stiffening device comprises a first actuator,
whereby the rope-tensioning device is designed to change the rope tension by means of the first actuator.

8. The exoskeleton according to claim 7,
whereby the first actuator is a pneumatic cylinder, a pneumatic muscle, or an electric motor.

9. The exoskeleton according to claim 8, furthermore comprising:
a sensor arrangement to measure in particular an angle or a force;
a controller;
whereby the controller is configured to control the first actuator of the rope-tensioning device on the basis of sensor data from the sensor arrangement so that, depending on the situation, the rope tension of the stiffening device can be adapted.

10. The exoskeleton according to claim 1,
whereby the back part and the pelvic support member are rotatably connected around a first axis of rotation, which stands orthogonally on the surface of the back part.

11. The exoskeleton according to claim 1,
whereby the back part and the pelvic support member are rotatably connected around a second axis of rotation, which runs diagonally to the main direction of the back part in the area of the back part.

12. The exoskeleton according to claim 7,
whereby the exoskeleton furthermore comprises a second actuator,
whereby the second actuator comprises a first and a second end,
whereby the first end of the second actuator is connected with the back part,
whereby the second end of the second actuator is connected with the pelvic support member,
whereby the second actuator is designed to support the movement between the back and the pelvis.

13. The exoskeleton according to claim 1,
whereby at least the first flexible-area back member consists of carbon-fiber-reinforced plastic.

14. The exoskeleton according to claim 1,
whereby the exoskeleton comprises a shoulder arrangement,
whereby a shoulder arrangement comprises the shoulder member, a first shoulder coupling member, a second shoulder coupling member, and the armrest,
whereby the first shoulder coupling member is connected with the shoulder member by means of a first axis of rotation,
whereby the first shoulder coupling member is connected with the second shoulder coupling member by means of a second axis of rotation,
whereby the second shoulder coupling member is connected with the armrest by means of a third axis of rotation,
whereby the first axis of rotation and the second axis of rotation are arranged at a right angle and at a distance from each other,
whereby the second axis of rotation and the third axis of rotation intersect.

15. The exoskeleton according to claim 14,
whereby the shoulder arrangement furthermore comprises a translational axis along the shoulder member,
whereby the first shoulder coupling member is movable along this translational axis.

16. The exoskeleton according to claim 14,
whereby the first axis of rotation is a tilting axis that is tiltable at an angle between 0° and 50°.

17. The exoskeleton according to claim 14,
whereby the angle between the second and the third axis of rotation is between 0° and 90°.

18. The exoskeleton according to claim 12, furthermore comprising:
a third actuator;
whereby the third actuator comprises a first end and a second end,
whereby the first end of the third actuator is connected with the armrest,
whereby the second end of the third actuator is connected with the second shoulder coupling member,
whereby the third actuator is designed to support the shoulder movement.

19. The exoskeleton according to claim 1, furthermore comprising:
a first part with a man-technology interface to transfer the force from and to a third body part to the first part and vice versa,
a second part with a man-technology interface to transfer force from and to the second part to a second body part and vice versa,
a coupling member, an actuating unit,
a sensor system, and
a controller,
whereby the first part is rotationally coupled to a second mechanical coupling,
whereby at least one of the first and the second mechanical couplings can be actuated by the actuating unit,
whereby the controller is designed to control the actuating unit on the basis of results measured by the sensor system.

20. The exoskeleton according to claim 19, whereby the first body part and the second body part are connected by means of a single extremity joint, in particular a shoulder joint, whereby the first body part and the second body part are in particular an arm and a pelvis/a hip of the same person.

21. The exoskeleton according to claim 19, whereby the second mechanical coupling is a rotatory coupling with at least one degree of freedom.

22. The exoskeleton according to claim 21, whereby the rotatory coupling comprises a parallelogram coupling component or a trapezoid coupling component.

23. The exoskeleton according to claim 21, whereby the rotatory coupling comprises at least one up-down component relative to the standing human body.

24. The exoskeleton according to claim 21, whereby the rotatory coupling comprises at least one forward-backward component relative to the standing human body.

25. The exoskeleton according to claim 19, whereby the second mechanical coupling comprises a translational coupling component along a trajectory.

26. The exoskeleton according to claim 25, whereby the trajectory comprises a straight line segment.

27. The exoskeleton according to claim 25, whereby the trajectory comprises a circular arc segment.

28. The exoskeleton according to claim 25, whereby the trajectory mimics a human anatomical movement.

29. The exoskeleton according to claim 19, whereby one of the first part and one of the second part comprise a supporting arrangement that mimics a spine.

30. The exoskeleton according to claim 19, whereby the device comprising at least a device for the production of rotatory and/or translational displacements and/or movements of the human biomechanics adapted to the anatomical characteristics of at least the area of the person to be supported and/or for the transfer of the forces around body areas to be supported and/or for the transfer and/or absorption of the forces of strained body areas.

31. The exoskeleton according to claim 29, whereby the device comprises at least one, in particular a plurality, in particular two force application points and/or areas between man and technology that facilitate a targeted transfer of force from one human structure to another human structure by means of the technical system, in order to specifically transfer the existing forces along one and/or more identical and/or different force paths, which can be switched individually and/or separately by means of the parallel structure of the technical elements.

32. The exoskeleton according to claim 19, whereby a specific adjustment motion is made possible by the actuators arranged in the axes or by the actuators driven on the device by means of a pulley-like construct, whereby all driven axes are preferably arranged so that they counteract gravity.

33. The exoskeleton according to claim 19, whereby the man-technology interface for the transfer of the force from a human to the technical structure or from a technical to a human structure is configured with different forms and different materials as well as the possible interface(s) to at least one device for the production of rotatory and/or translational movements and/or other parallel arranged devices for the transfer of force.

34. The exoskeleton according to claim 19, whereby active actuating elements are integrated in the device, which comprise at lease a control option in the form of at least one switch to consent to at least an individual control of a form of movement of the movements made possible by the device for the production of rotatory and/or translational human movements and for the targeted transfer of force or at least one sensor that provides data about the strain and/or for the determination of at least one movement of at least one human body area that is processed in the controller to control the elements of the device accordingly.

35. The exoskeleton according to claim 19, whereby components of the device are directly or indirectly connected with the connecting members to ensure the relative arrangement and to be able to control passively and/or actively with interfaces and/or connecting members with at least one characteristic, whereby this characteristic is either determined geometrically and/or allows for an adaptation.

36. The exoskeleton according to claim 19, whereby the device comprises at least an actuator for the realization of predetermined adjustment forces and/or strain and movement-dependent adjustment forces to passively and/or actively modify the characteristic of the device such as the level of support and/or the joint angles preventively and/or operatively to the strain and movement states.

37. The exoskeleton according to claim 19, whereby the device is configured for the targeted and controllable stabilization, stiffening, or activation of at least one soft or elastic technical or biomechanical structure and/or of technical or biomechanical elements so that forces can be transferred in the direction of the main strain while remaining flexible in the main direction of the movement.

38. The exoskeleton according to claim 19, whereby at least a possibility for the integration of sensors for the direct or indirect measurement of at least a strain on an area of the human body and/or the human movement is integrated, to realize a targeted control by means of the data captured accordingly.

39. The exoskeleton according to claim 19, whereby at least a reference element for the determination of a defined position between the device and the device carrier, whereby at least an arresting member is present to fasten the device to at least one body part of the person wearing the device.

40. An exoskeleton system, comprising:
a shoulder member;
at least one armrest;

a pelvic support member;
a back part with a first end and a second end;
whereby the back part comprises at least a first flexible-area back member with a first and a second end and at least a first stiffening device with a first stiffening means,
whereby the first flexible-area back member is oriented so that its first end faces the first end of the back part and its second end faces the second end of the back part,
whereby the first end of the back part is attached to the shoulder member,
whereby the second end of the back part is attached to the pelvic support member, whereby the armrest is directly or indirectly articulated to the shoulder member,
whereby the first stiffening means is designed so that the first flexible-area back member is specifically stiffened in a bending direction, wherein the shoulder member, at least one armrest, pelvic support member, or a back part with a first end and a second end form a modular architecture that can be reconfigured,
whereby at least one protruding retaining structure is arranged on the surface of the flexible-area back member facing away from the back part, on which the stiffening means of the stiffening device rests, so that the stiffening means is located at a distance from the surface of the flexible-area back member.

* * * * *